United States Patent [19]

Kida

[11] Patent Number: 5,731,466
[45] Date of Patent: Mar. 24, 1998

[54] METHOD FOR PREPARING ALKYLBENZOIC ACID

[75] Inventor: Koichi Kida, Tsukuba, Japan

[73] Assignee: Mitsubishi Gas Chemical Company, Inc., Tokyo, Japan

[21] Appl. No.: 732,606

[22] Filed: Oct. 16, 1996

[30] Foreign Application Priority Data

Nov. 1, 1995 [JP] Japan .................................. 7-285115
Nov. 1, 1995 [JP] Japan .................................. 7-285116

[51] Int. Cl.$^6$ ................................................. C07C 51/16
[52] U.S. Cl. ............................................ 562/414; 562/416
[58] Field of Search ........................................... 562/414

[56] References Cited

U.S. PATENT DOCUMENTS

| | | | |
|---|---|---|---|
| 2,712,551 | 7/1955 | Himel | 562/414 |
| 3,088,974 | 5/1963 | Cier | 562/414 |
| 3,607,920 | 9/1971 | Clark | 562/414 |

*Primary Examiner*—Michael L. Shippen
*Attorney, Agent, or Firm*—Frishauf, Holtz, Goodman, Langer & Chick, P.C.

[57] ABSTRACT

A method for preparing an alkylbenzoic acid is herein disclosed which comprises subjecting an alkylbenzene having at least two alkyl groups of 1 to 3 carbon atoms to a liquid phase oxidative reaction with a molecular oxygen-containing gas in the presence of a soluble heavy metal catalyst to convert one alkyl group into a carboxylic acid, thereby preparing the alkylbenzoic acid, and impurities contained in the alkylbenzene recovered from the reaction solution are removed therefrom by distillation, water washing, alkali washing, a treatment with an anion exchange resin or a treatment with a solid adsorbent, and the impurities-free fraction is reused as a raw material.

Furthermore, the conversion of the desired product is regulated to 25% or less in the liquid phase oxidative reaction, whereby the reaction is carried out in a boiling heat removal state and reaction heat is removed as the heat of vaporization.

Thus, there can be decreased a dicarboxylic acid secondarily produced during the manufacture of the alkyl-benzoic acid which is a monocarboxylic acid by subjecting the alkylbenzene to the liquid phase oxidation, whereby problems such as the trouble of equipment operation and the deterioration of product quality can be solved.

8 Claims, No Drawings

METHOD FOR PREPARING ALKYLBENZOIC ACID

BACKGROUND OF THE INVENTION

(1) Field of the Invention

The present invention relates to a method for preparing an alkylbenzoic acid by subjecting an alkyl-benzene to a liquid phase oxidation. More specifically, it relates to a method for solving problems such as the trouble of equipment operation and the deterioration of quality owing to a dicarboxylic acid secondarily produced during the manufacture of the alkylbenzoic acid.

(2) Description of the Prior Art

Some methods for preparing a benzoic acid are known from U.S. Pat. Nos. 2,712,549 and 2,712,551 as well as Japanese Patent Publication Nos. 46217/1977 and 8816/1981, and each of these known methods comprises oxidizing an alkylbenzene typified by xylene, mesitylene or the like with a molecular oxygen-containing gas in a liquid phase in the presence of a soluble heavy metal catalyst to convert one alkyl group into a carboxyl group.

In the above-mentioned U.S. patents, when toluic acid is obtained by oxidizing xylene, toluic acid is further oxidized simultaneously, whereby phthalic acid which is insoluble in a reaction solution is secondarily produced. The thus secondarily produced phthalic acid is then deposited on the heat transfer surface of a heat exchanger for removing the heat of the oxidative reaction, so that the removal of the heat is impossible. In addition, there is another problem that toluic acid is contaminated with phthalic acid when toluic acid is collected by crystallization separation.

For the purpose of solving the former problem of the heat removal, there has been employed a technique which comprises flushing the reaction solution to remove the heat, but in the industrial practice of this technique, it is necessary to install a flush tank and its process is also complex, and hence the occurrence of some additional troubles can be predicted. With regard to the latter problem of the contamination with phthalic acid, phthalic acid has been removed by filtering the reaction solution while it is hot. In this method, however, phthalic acid dissolved in the reaction solution cannot be removed therefrom. In consequence, when toluic acid is obtained in the form of crystals by cooling, it can not be avoided that the toluic acid product is contaminated with a fair amount of phthalic acid.

SUMMARY OF THE INVENTION

An object of the present invention is to provide a method for solving problems such as the trouble of equipment operation and the deterioration of quality due to a dicarboxylic acid secondarily produced during the manufacture of an alkylbenzoic acid which is a monocarboxylic acid by subjecting an alkylbenzene to a liquid phase oxidation.

The present inventors have intensively investigated to solve the above-mentioned problems, and as a result, it has been supposed that many peaks of impurities are observed in an alkylbenzene recovered after an oxidative reaction by gas chromatography and some of these impurities promote the secondary production of a dicarboxylic acid. That is to say, in view of a fact that the amount of the dicarboxylic acid gradually increases when the unreacted alkylbenzene is recovered and then reused as a raw material, it has been found that the secondary production of the dicarboxylic acid can be inhibited by removing, prior to reusing the unreacted alkylbenzene as a raw material, the impurities contained in this unreacted alkylbenzene subjected to the oxidative reaction and then recovered.

That is to say, the first aspect of the present invention is directed to a method for preparing an alkylbenzoic acid which comprises subjecting an alkylbenzene having at least two alkyl groups of 1 to 3 carbon atoms to a liquid phase oxidative reaction with a molecular oxygen-containing gas in the presence of a soluble heavy metal catalyst to convert one alkyl group into a carboxyl group, thereby preparing the alkylbenzoic acid, said method comprising the steps of distilling a reaction solution to recover an unreacted alkylbenzene fraction, removing impurities contained in the unreacted alkylbenzene fraction therefrom by at least one of the following means, and then reusing the impurities-free alkylbenzene fraction as a raw material:

(1) washing the alkylbenzene fraction with water, (2) washing the alkylbenzene fraction with an aqueous alkali solution of pH 8 to 14, (3) distilling the alkylbenzene fraction again in a distillation column having 10 or more theoretical steps, (4) bringing the alkylbenzene fraction into contact with an anion exchange resin, (5) bringing the alkylbenzene fraction into contact with a solid adsorbent, and (6) bringing the alkylbenzene fraction into contact with an alkali solid.

Furthermore, the present inventors have found the following facts. That is to say, it is important to inhibit the production itself of the dicarboxylic acid in the oxidative reaction to the utmost. In view of a relation between the conditions of the oxidative reaction and the production of the dicarboxylic acid. By reducing a reaction pressure to carry out vaporization heat removal in the boiling state and controlling the conversion of the alkylbenzene as the raw material at a low level, the production ratio of the dicarboxylic acid can be lowered. And then the temperature can be adjusted smoothly since heat removal is not done by cooling. In addition, since the production of the dicarboxylic acid can be inhibited, any trouble does not occur even during the purification by distillation, so that the high-purity alkylbenzoic acid can be obtained in a high yield.

Thus, the second aspect of the present invention is directed to a process which comprises the steps of carrying out the above-mentioned liquid phase oxidative reaction controlling a conversion to 25% or less, whereby reacting in boiling heat removal state to remove reaction heat as the heat of vaporization. The removal of the reaction heat is preferably accomplished in a manner which comprises continuously feeding water to a reaction vessel for the liquid phase oxidation to cause the azeotropy of water and an alkylbenzene, or another manner which comprises causing the azeotropy of water and the alkylbenzene, while the amount of an aqueous phase drawn from a condensed reflux liquid of a boiling steam is regulated.

DETAILED DESCRIPTION OF THE INVENTION

An alkylbenzene which can be used as a raw material has 2 to 6 substituents on a benzene nucleus, and each of at least 2 substituents has an alkyl group having 1 to 3 carbon atoms. In the present invention, methylbenzenes such as orthoxylene, metaxylene, paraxylene, mesitylene and pseudocumene can particularly suitably be used as the alkylbenzenes, and corresponding orthotoluic acid, metatoluic acid, paratoluic acid, 3,5-dimethylbenzoic acid and 3,4-dimethylbenzoic acid can be prepared as alkylbenzoic acids.

For the oxidative reaction of the alkylbenzene, a known method can be applied. As a reaction solvent, a less oxidizable solvent such as benzene may be used, but it is preferable that the alkylbenzene itself which is the raw material is used as the solvent. As heavy metal catalysts which are soluble in the solvent, organic acid salts of cobalt, manganese, cerium and the like are effective, and suitable examples of such heavy metal catalysts include cobalt naphthenate, manganese naphthenate and cobalt toluylate. The metal concentration of the catalyst in a reaction solution is in the range of 10 to 3000 ppm, preferably 30 to 300 ppm.

An oxidative reaction temperature is usually in the range of 100° to 200° C., preferably 120° to 180° C., depending upon on the kind of selected alkylbenzene. A pressure which can be employed in the present invention is such as to be not less than a pressure under which the reaction solution can keep up a liquid phase at the reaction temperature, and it is preferably in the range of 1 to 20 $Kg/cm^2G$, more preferably 2 to 10 $Kg/cm^2G$.

As a molecular oxygen-containing gas, air is usually used, and air is blown into the reaction system so that oxygen may sufficiently disperse therein. Moreover, in order to avoid explosion, the amount of air to be blown is controlled so that an oxygen concentration in an exhaust gas in a steady state at the exit of the reaction vessel may be 6% or less.

The reaction can be allowed to proceed by a batch system, a semi-batch system or a continuous system using a tank type reaction vessel equipped with a stirrer, but for an industrial purpose, it is preferable to carry out the reaction by the continuous system.

For the above-mentioned oxidative reaction, the alkylbenzene as the raw material is fed to an oxidative reaction vessel together with the recovered alkylbenzene. The recovered alkylbenzene fraction can be used as the raw material for the reaction again without being subjected to any treatment, but in fact, as the number of the recycle of the alkylbenzene increases, the production of a dicarboxylic acid gradually increases, as described above.

This reason would be that impurities which promote the secondary production of the dicarboxylic acid are accumulated in the recycled alkylbenzene, and as described above, many peaks of the impurities can be confirmed in the recycled alkylbenzene by gas chromatography.

As a first technique for removing the impurities contained in the alkylbenzene recovered by the first aspect of the present invention, there is a means in which the impurities can be removed by water washing. According to this means, 300 to 10 parts, preferably 100 to 30 parts of water is sufficiently brought into contact with and mixed with 100 parts of the alkylbenzene fraction which has undergone the reaction of the raw material recycle, and the resulting aqueous layer is then separated by decanter. The resulting alkylbenzene layer can then be subjected to the oxidative reaction, whereby the secondary production of the dicarboxylic acid can be inhibited.

Furthermore, the means of alkali washing is also effective. According to this alkali washing means, 100 to 0.1 part, preferably 50 to 3 parts of the aqueous alkaline solution having a pH of 8 to 14 is sufficiently brought into contact with and mixed with 100 parts of the alkylbenzene fraction, the resulting aqueous alkali layer is drawn out and the recovered alkylbenzene can be fed to the oxidative reaction. Examples of the usable alkali include inorganic alkalis such as caustic soda, caustic potash, sodium carbonate, sodium bicarbonate and an aqueous ammonia solution. In addition, aqueous solutions of amines can also exert the similar effect, but higher amines which are easily soluble in an organic layer is not so preferable.

Instead of the water washing, redistillation is also effective. Such an alkylbenzene fraction as mentioned above can be rectified in a distillation column having 10 or more theoretical steps to concentrate the purity of the alkylbenzene to 98% or more, and the thus concentrated alkylbenzene can be then fed again to the oxidative reaction. In this case, the secondary production of the dicarboxylic acid is as low as in the case of the fresh raw material.

In addition, it is also effective to directly pour an alkaline solid into the alkylbenzene fraction without using any aqueous solution. In this case, the recovered alkylbenzene can be brought into contact with an insoluble inorganic alkali such as solid caustic soda, caustic potassium, calcium oxide or magnesium oxide, whereby the alkylbenzene raw material which reduces the secondary production of the dicarboxylic acid can be obtained.

Similarly, an anion exchange resin, for example, a trade name Amberlite A-400 or Dowex 1-XI made of Tokyo Organic Chemistry Co., Ltd. is effective. In addition, it is also effective to bring the alkylbenzene fraction into contact with a usual solid adsorbent, and for example, activate carbon, active alumina, silica gel and zeolite are effective as the solid adsorbent. Each of these treating agents can be stirred together with the alkylbenzene in a solid-liquid system to mix them. Alternatively, it may be used in the form of a fixed bed, and in this case, an optional industrial contact manner such as the continuous passage of the alkylbenzene through the fixed bed can be utilized. Incidentally, the amount of the alkali solid, the anion exchange resin or the solid adsorbent can suitably be decided in consideration of the volume of the respective materials to be used.

When the impurities contained in the alkylbenzene recovered from the reaction solution are removed therefrom by the method of the present invention and the recovered alkylbenzene is then reused as the raw material, the production of the dicarboxylic acid can be inhibited as low as the first alkylbenzoic acid production level, as shown in Examples 1 to 4 which will hereinafter be described.

The second aspect of the present invention is directed a process which comprises the steps of carrying out the above-mentioned liquid phase oxidative reaction controlling a conversion to 25% or less, whereby reacting in boiling heat removal state to remove reaction heat as the heat of vaporization. According to this method, the production of the dicarboxylic acid in the oxidative reaction can be inhibited in accordance with a relation between the conditions of the oxidative reaction and the production of the dicarboxylic acid, with the result that a temperature adjustment can smoothly be accomplished.

The boiling heat removal state is not a strict boiling point of the reaction solution but a state in which reaction heat by blown air harmonizes with vaporization heat by vapor accompanied by an exhaust gas at a specific temperature and pressure. In fact, in order to bring the reaction solution containing a large excess of the alkylbenzene having a high boiling point into the boiling heat removal state, a reaction pressure is in the vicinity of atmospheric pressure and a reaction rate often lowers. Then, when an azeotropic state of the alkylbenzene and water is caused by continuously pouring water into the reaction vessel, the boiling point can drop, and the reaction can proceed at a sufficiently high reaction rate under a heightened pressure.

Poured water vaporizes together with water originally produced by the oxidization, and then condensed by a reflux condenser. Thus, an oil phase alone is refluxed through the reaction vessel, and an aqueous phase is drawn out of the reaction system. In consequence, water is not accumulated in the reaction solution.

Instead of the pouring of water, all of water produced by the oxidization is not drawn out from the condensed liquid and a part of water may be refluxed. The amount of water to be poured into the reaction vessel or water to be refluxed depend upon the quantity of dissipated heat and the rate of the oxidative reaction, and therefore such an amount of water should be stably adjusted by a predetermined temperature and pressure.

From the reaction solution in which the reaction has been completed, the unreacted alkylbenzene and the produced alkylbenzoic acid can be recovered by distillation, or alternatively the reaction solution can be first cooled to crystallize the alkylbenzoic acid, whereby the produced alkylbenzoic acid can be separated, and the unreacted alkylbenzene can be then recovered by the distillation.

If the conversion of the alkylbenzene is in excess of about 30%, the crystals of the dicarboxylic acid precipitate at the reaction temperature. In this case, therefore, it is necessary that the reaction solution in which the reaction has been completed should be filtered at a hot time to remove the dicarboxylic acid crystals. On the contrary, if the conversion of the alkylbenzene as the raw material is regulated to 25% or less by the second aspect of the present invention, this filtration at the hot time is unnecessary, which can simplify the process.

As described above, according to the method of the present invention, the impurities contained in the unreacted alkylbenzene recovered after the oxidative reaction can be removed therefrom prior to its reuse, and the conversion of the alkylbenzene as the raw material is controlled to a low level, whereby vaporization heat removal can be carried out in the boiling state in the reaction solution. In consequence, some problems, for example, a trouble of equipment operation such as the heat removal in the reaction vessel and the deterioration of a product quality by the contamination of the product with the dicarboxylic acid can be solved.

Furthermore, according to the method of the present invention, the content of the dicarboxylic acid in the reaction production is low, and therefore the flowability of a liquid on a tower bottom is good and so a trouble such as the draw of a bottom residue is not present. In consequence, the yield of the alkylbenzoic acid is high. Since the dicarboxylic acid is not included in the alkylbenzoic acid which is the product, the high-purity alkylbenzoic acid can easily be obtained by distillation purification.

Next, the present invention will be described in more detail with reference to examples. However, the scope of the present invention is not limited to these examples.

EXAMPLE 1

150 g of metaxylene as a raw material and 0.5 g of cobalt naphthenate as a catalyst were placed in a 500-ml autoclave having a stirrer made of SUS316, and the pressure in the autoclave was heightened to 5 Kg/cm$^2$G with a nitrogen gas. Afterward, the solution was heated up to 140° C. While a reaction pressure was maintained at 10 Kg/cm$^2$G, air was blown into the autoclave at about 50 liters/hr (in terms of atmospheric pressure) so that an exit oxygen concentration was not in excess of 6%. At this time, the rotational speed of stirring blades was controlled to 1000 rpm so that sufficient gas contact might be accomplished. While a reaction temperature was maintained at 140° to 150° C., reaction was carried out for 2 hours.

After the reaction, a product was cooled to room temperature and then taken out, and in the thus obtained product, a small amount of a white precipitate was contained. Analysis was made, and it was apparent that the amount of this white precipitate was 4.1 g and 87% by weight of isophthalic acid was included in the precipitate. The amount of isophthalic acid dissolved in the reaction solution was 0.3 g, and the amount of produced isophthalic acid was 3.9 g in all. With regard to the results of this reaction, the conversion of metaxylene was 37.5%, and the selectivity of metatoluic acid was 73.5 mol %. The selectivity of produced isophthalic acid to metaxylene consumed in the reaction was 5.4 mol %.

The substantially total amount of the reaction solution was distilled under a reduced pressure of 100 mmHg to recover 87 g of a metaxylene fraction. Next, 70 g of recovered metaxylene was partially taken out and then mixed with fresh metaxylene to prepare 150 g of a raw material again, and an oxidative reaction was carried out under all the same conditions as described above. This operation was repeated, and after the 4th reaction, 70 g of a metaxylene fraction was placed in a separatory funnel. Afterward, 70 g of water was added thereto, and the solution was then vigorously shaken. After the resulting aqueous phase was drawn out, the solution was subjected to the 5th oxidative reaction again.

The reaction results of this example are shown in Table 1. It is apparent that the production of isophthalic acid is inhibited by the water washing and its content is as low as the first production level.

TABLE 1

| Times of Reaction | Conversion of Metaxylene (%) | Selectivity of m-Toluic Acid (mol %) | Selectivity of Iso-phthalic Acid (mol %) |
| --- | --- | --- | --- |
| 1 | 37.5 | 73.5 | 5.4 |
| 2 | 38.7 | 72.2 | 6.1 |
| 3 | 36.3 | 73.4 | 6.9 |
| 4 | 39.2 | 71.5 | 7.6 |
| 5 (after water washing) | 38.1 | 71.2 | 5.3 |

EXAMPLES 2 TO 4

The conversion of an alkylbenzene by an oxidative reaction was regulated to a value of 35 to 40% as in Example 1, and reaction and recovery were repeatedly carried out. In the 5th reaction, the alkylbenzene recovered after the 4th reaction was washed with an aqueous alkali solution in Example 2 (5% NaOH was used in an amount of 10 g with respect to 70 g of paraxylene, and washing was done at room temperature), it was treated with an anionic exchange resin (Amberlite 400 was used in an amount of 10 g with respect to 70 g of orthoxylene, and the treatment was made at 50° C.) in Example 3, and it was treated with a solid adsorbent (active carbon Turumicoal was used in an amount of 5 g with respect to 70 g of mesitylene, and the treatment was made at 60° C.) in Example 4. Afterward, the thus treated alkylbenzene was further subjected to the reaction.

The reaction results of the respective examples are shown in Table 2. It is apparent that the production of dicarboxylic acid is inhibited as low as the first production level.

TABLE 2

| Raw Material | Example 2 Paraxylene | Example 3 Orthoxylene | Example 4 Mesitylene |
|---|---|---|---|
| *Results of First Reaction* | | | |
| Conversion of Raw Material (%) Selectivity (mol %) | 35.1 | 35.7 | 40.2 |
| Monocarboxylic Acid | 72.4 | 69.5 | 61.2 |
| Dicarboxylic Acid | 4.7 | 5.2 | 8.5 |
| *Results of 4th Reaction* | | | |
| Conversion of Raw Material (%) Selectivity (mol %) | 36.0 | 38.2 | 41.1 |
| Monocarboxylic Acid | 71.5 | 70.1 | 59.8 |
| Dicarboxylic Acid | 8.2 | 8.5 | 11.3 |
| *Results of 5th Reaction* | | | |
| Conversion of Raw Material (%) Selectivity (mol %) | 35.5 | 38.0 | 40.5 |
| Monocarboxylic Acid | 71.2 | 69.8 | 60.3 |
| Dicarboxylic Acid | 4.3 | 5.3 | 8.0 |

EXAMPLE 5

200 g of metaxylene as a raw material and 0.5 g of cobalt naphthenate (Co: 6% by weight) as a catalyst were placed in a one-liter autoclave having a reflux condenser, a stirrer and an air blowing tube made of SUS316, and the pressure in the autoclave was heightened to 5 Kg/cm$^2$G with a nitrogen gas. Afterward, the solution was heated up to 150° C. While a reaction pressure was maintained at 5 Kg/cm$^2$G, air was blown into the autoclave at about 70 liters/hr (in terms of atmospheric pressure) so that an exit oxygen concentration was not in excess of 6%. At this time, the rotational speed of stirring blades was controlled to 800 rpm so that sufficient gas contact might be accomplished.

Next, water was added to the reaction vessel at a feed rate of about 30 g/hr via an air blowing line by the use of a metering pump so that reaction temperature might be maintained at 155° to 160° C., and reaction was then carried out for one hour. During this reaction, when a reaction pressure was heightened, the reaction temperature immediately rose, and when the pressure was reduced, the reaction temperature also lowered correspondingly. Thus, it was confirmed that the solution was in a boiling state under these reaction conditions. The total amount, i.e., 36 g of added water and water produced by an oxidative reaction was continuously drawn out through a lower pot of the reflux condenser.

After the reaction, the resulting product was taken out and then analyzed, and as the result, the conversion of metaxylene which was the raw material was 18.5%. The selectivity of metatoluic acid which was the desired product was 72.5 mol %, and the selectivity of isophthalic acid which was a dicarboxylic acid was 1.9 mol %.

This reaction solution was directly distilled in a distillation column under a reduced pressure of 200 mmHg, whereby metaxylene and a low-boiling fraction were distilled off. Afterward, 32 g of a metatoluic acid fraction was obtained at 150° to 160° C. under a reduced pressure of 15 mmHg (yield=93%). In this fraction, isophthalic acid was not detected, and the purity of metatoluic acid was 98.2% by weight.

Next, 140 g of distilled metaxylene was taken and then mixed with 60 g of fresh metaxylene to prepare 200 g of a raw material again, and an oxidative reaction was then carried out under all the same conditions as described above. This procedure was repeated, and after the 4th reaction, 140 g of a metaxylene fraction was placed in a separatory funnel. Afterward, 70 g of water was added thereto, and the solution was then vigorously shaken. After the resulting aqueous phase was drawn out, the solution was subjected to the 5th oxidative reaction again.

The reaction results of this example are shown in Table 3. It is apparent that the production of isophthalic acid is inhibited by the water washing and its content is as low as the first production level.

TABLE 3

| Times of Reaction | Conversion of Metaxylene (%) | Selectivity of m-Toluic Acid (mol %) | Selectivity of Iso-phthalic Acid (mol %) |
|---|---|---|---|
| 1 | 18.5 | 72.5 | 1.9 |
| 2 | 19.1 | 71.6 | 2.2 |
| 3 | 18.3 | 72.6 | 2.8 |
| 4 | 19.4 | 73.3 | 3.4 |
| 5 (after water washing) | 19.2 | 72.4 | 1.8 |

COMPARATIVE EXAMPLE 200 g of metaxylene as a raw material and 0.5 g of cobalt naphthenate (Co: 6% by weight) as a catalyst were placed in a one-liter autoclave having a reflux condenser, a stirrer and an air blowing tube made of SUS316, and the pressure in the autoclave was heightened to 5 Kg/cm$^2$G with a nitrogen gas. Afterward, the solution was heated up to 150° C. While the reaction pressure was maintained at 10 Kg/cm$^2$G, air was blown into the autoclave at about 70 liters/hr (in terms of atmospheric pressure) so that an exit oxygen concentration was not in excess of 6%. At this time, the rotational speed of stirring blades was controlled to 800 rpm so that sufficient gas contact might be accomplished.

Next, the temperature of a heating medium in a jacket of the autoclave was regulated so that a reaction temperature might be maintained at 155° to 160° C., and reaction was then carried out for 2 hours. The total amount, i.e., 12 g of water produced by an oxidative reaction was continuously drawn out through a lower pot of the reflux condenser.

After the reaction, the resulting product was taken out and then analyzed, and as the result, the conversion of metaxylene which was the raw material was 27.9%. The selectivity of metatoluic acid which was the desired product was 74.2 mol %, and the selectivity of isophthalic acid which was a dicarboxylic acid was 4.4 mol %.

On a cooling surface of the inside wall of the autoclave, white isophthalic acid was deposited. This reaction solution was directly distilled in a distillation column under a reduced pressure of 200 mmHg, whereby metaxylene and a low-boiling fraction were distilled off. Afterward, 45 g of a metatoluic acid fraction was obtained at 150° to 160° C. under a reduced pressure of 15 mmHg (yield=85%). At the end of this distillation, the viscosity of the solution in the distillation column rose owing to the remaining isophthalic acid, so that a substantial amount of metatoluic acid avoidably remained on the bottom of the distillation column, with the result that its yield lowered. In addition, the fluidity of the residue on the column bottom was low, so that the addition of a solvent and the operation of reheating were required in order to fluidize and then draw out the residue.

In the case that a conversion is increased so as to be higher than 25% as compared with Example 5 and the boiling heat removal is not carried out, the production of the dicarboxylic acid increases as described above. Furthermore, in order to prevent the yield of metatoluic acid from lowering in the distillation, the hot filtration is necessary.

What is claimed is:

1. A method for preparing an alkylbenzoic acid which comprises subjecting an alkylbenzene having at least two alkyl groups of 1 to 3 carbon atoms to a liquid phase oxidative reaction with a molecular oxygen-containing gas in the presence of a soluble heavy metal catalyst to convert one alkyl group into a carboxyl group, thereby preparing the alkylbenzoic acid, said method comprising the steps of distilling a reaction solution to recover an unreacted alkylbenzene fraction, removing impurities contained in the unreacted alkylbenzene fraction therefrom by at least one of the following means, and then reusing the impurities-free alkylbenzene fraction as a raw material:

(1) washing the alkylbenzene fraction with water, (2) washing the alkylbenzene fraction with an aqueous alkali solution of pH 8 to 14, (3) distilling the alkylbenzene fraction again in a distillation column having 10 or more theoretical steps, (4) bringing the alkylbenzene fraction into contact with an anion exchange resin, (5) bringing the alkylbenzene fraction into contact with a solid adsorbent, and (6) bringing the alkylbenzene fraction into contact with an alkali solid.

2. The preparation method of an alkylbenzoic acid according to claim 1 wherein the conversion of the alkylbenzene by the liquid phase oxidative reaction is 25% or less.

3. The preparation method of an alkylbenzoic acid according to claim 1 wherein the liquid phase oxidative reaction is carried out in a boiling heat removing state, and reaction heat is removed as the heat of vaporization.

4. The preparation method of an alkylbenzoic acid according to claim 3 wherein while water is continuously fed to a liquid phase oxidative reaction vessel, the reaction heat is removed in the azeotropic state of water and the alkylbenzene.

5. The preparation method of an alkylbenzoic acid according to claim 3 wherein while the amount of an aqueous phase drawn from the condensed reflux liquid of a boiling steam is regulated, the reaction heat is removed in the azeotropic state of water and the alkylbenzene.

6. The preparation method of an alkylbenzoic acid according to claim 2 wherein the liquid phase oxidative reaction is carried out in a boiling heat removing state, and reaction heat is removed as the heat of vaporization.

7. The preparation method of an alkylbenzoic acid according to claim 6 wherein while water is continuously fed to a liquid phase oxidative reaction vessel, the reaction heat is removed in the azeotropic state of water and the alkylbenzene.

8. The preparation method of an alkylbenzoic acid according to claim 6 wherein while the amount of an aqueous phase drawn from the condensed reflux liquid of a boiling steam is regulated, the reaction heat is removed in the azeotropic state of water and the alkylbenzene.

* * * * *